(12) United States Patent
McKeon

(10) Patent No.: US 7,618,794 B2
(45) Date of Patent: Nov. 17, 2009

(54) METHOD FOR CONTROLLING ENVIRONMENTAL ALLERGENS

(76) Inventor: John McKeon, 47 Merrion Square, Dublin (IE)

( * ) Notice: Subject to any disclaimer, the term of this patent is extended or adjusted under 35 U.S.C. 154(b) by 413 days.

(21) Appl. No.: 10/490,782

(22) PCT Filed: Sep. 25, 2002

(86) PCT No.: PCT/IE02/00138

§ 371 (c)(1),
(2), (4) Date: Aug. 4, 2004

(87) PCT Pub. No.: WO03/036254

PCT Pub. Date: May 1, 2003

(65) Prior Publication Data

US 2004/0255983 A1     Dec. 23, 2004

(30) Foreign Application Priority Data

Sep. 25, 2001 (IE) ............................. S2001/0850

(51) Int. Cl.
*C12Q 1/24* (2006.01)
*C12Q 1/02* (2006.01)
*C12Q 1/04* (2006.01)
*A61K 39/35* (2006.01)

(52) U.S. Cl. ............................. 435/30; 435/32; 435/34; 424/77; 424/275.1; 424/402

(58) Field of Classification Search ........................ None
See application file for complete search history.

(56) References Cited

FOREIGN PATENT DOCUMENTS

| DE | 199 29 856 A1 | 1/2001 |
|---|---|---|
| WO | WO/98/55807 | 12/1998 |
| WO | WO/01/13962 A1 | 3/2001 |

OTHER PUBLICATIONS

Bishoff et al, Clinical and Experimental Allergy 28: 60-65, 1998.*
McDonald, J Allergy Clin Immunol 90(4): 599-608, 1992.*
Nagakura et al, Clin Exp Allergy 26(5): 585-9, May 1996.*
Vaughan et al, J Allergy Clin Immunol 103: 227-231, 1999.*

* cited by examiner

*Primary Examiner*—Phuong Huynh
(74) *Attorney, Agent, or Firm*—Tod R. Nissle, P.C.

(57) ABSTRACT

There is provided a method for controlling environmental allergens in articles including toys, bedding, clothing and the like that tend to collect house dust mite and other allergens. One method involves seeding an article with house dust mites, exposing the article to conditions that promote accelerated growth of house dust mites (10, block 100), washing the article to remove house dust mites (20, block 200), testing the washed article to determine that the level of dust mite remaining in the washed article is below a predetermined level (50, block 200), repeating the washing step a number of times approximating the number of washes the article is expected to undergo during its normal useful lifetime (20, block 200) and finally passing the article through a series of quality control tests (30 and 40 block 300) so that the article may be assured as washable to control its mite and allergen levels without loss of integrity and safety over a plurality of wash cycles.

6 Claims, 6 Drawing Sheets

METHOD FOR CONTROLLING ENVIRONMENTAL ALLERGENS

The present invention relates to a method for controlling environmental allergens and in particular to a testing procedure for ensuring that low levels of environmental allergens are present when the starting components of an article are assembled to form an article and also that low levels of environmental allergens can be maintained in said articles.

People suffering from asthma may be allergic to a large range of environmental challenges including house dust mites, cockroaches, other animals, plants, pollen, moulds, chemicals or additives. Tiny indoor particles suspended in the air, although invisible to the naked eye, carry these substances and may trigger asthma attacks. These substances, called allergens, include the droppings of house dust mites and cockroaches, indoor mould spores and animal dander (the shed skin of pets such as cats and dogs). Allergens can build up in the home, worsening the frequency and severity of allergy and asthma symptoms.

The present invention relates to all common household allergens and whilst described particularly with reference to dust mites, it is to be understood that the scope of the invention includes also the above allergens.

The house dust mite was discovered to cause allergic disease in the early 1920s. Subsequently dust mite allergens have been linked to asthmatic reactions in humans. It is believed that the allergens cause an allergic reaction which can manifest itself in many ways. For example, it may result in inflammation of tissue at the surface of the bronchioles of the lungs causing breathing difficulties for an asthmatic person. Up to 80% of asthma sufferers have attacks that are triggered by the house dust mite and it's associated allergens.

The common name "house dust mite" refers to those mites found regularly in house dust. The two most common species are *Dermatophagoides pteronyssinus* and *Dermatophagoides farinae*. The most powerful allergens are found in the faecal matter produced by the mites. Allergen levels increase over time as the house dust mite naturally infests the household environment. In order for this to occur the house dust mite feeds on microscopic skin flakes and other household debris and excretes allergenic faecal pellets. Often the feces become colonised by fungi, which in turn may also produce allergens. Soft toys, clothing, soft furnishings, bedding and pillows provide established breeding grounds for the house dust mite as skin flakes and other debris become collected within spaces between textile fibres.

As mentioned above, cockroaches and their parts are allergenic. Commonly, these and/or other allergens combine with animal dander and hair and mite pellets to pose an even more allergenic challenge to susceptible individuals.

Medical experts advise that allergy and asthma sufferers should avoid the trigger factors that precipitate their symptoms. It is also recommended that the allergen levels within a household are kept below levels known to precipitate asthmatic reactions. Methods are known for the treatment of households and articles within households to reduce the house dust mite population and it's associated allergens as well as dog, cat and cockroach allergens. People in households with asthmatics or sufferers of allergic diseases often go to tremendous lengths to ensure that there is minimal contact with trigger factors. Unfortunately there are no standard conditions under which an article can be manufactured and tested to see if it can withstand enough treatments over its useful lifetime to maintain acceptably low levels of house dust mite and other allergens over that lifetime without losing quality.

The present invention seeks to alleviate the aforementioned problems.

Accordingly, the present invention provides a method for treating an article that tends to collect house dust mite or other allergens, the method comprising:
  a) seeding an article with a live house dust mite or other allergenic organism population;
  b) exposing the seeded article to environmental conditions that promote an accelerated growth of the population;
  c) washing the article to remove the population and associated allergens after accelerated growth;
  d) testing the washed article to determine the level of allergen and live allergenic organisms remaining and determining whether the remaining level is below a target level;
  e) if the level determined is below the target level, repeating step c) a plurality of times; and
  f) subjecting the article to quality integrity tests so that the article can be assured as washable to control its allergenic organism and allergen levels while retaining its integrity over a plurality of wash cycles. The article may be assured if it is found to retain its integrity over a number of wash cycles which would be typical for the number of washes the article would be expected to undergo during its normal, useful lifetime in a domestic environment.

The seeding step can be done in the artificial environment of the laboratory or in the natural domestic or work environment. The latter case may be used to determine the natural rate of allergen build-up in a particular environment.

The quality integrity tests may include:
  (a) colour fastness;
  (b) dimensional stability;
  (c) stitching failure; and
  (d) visual assessment tests.

An optional pre-test sequence may be employed to detect the presence of any of a number of recognised allergens and/or irritants remaining from the manufacture of the article, including but not limited to microbiological contaminants, formaldehyde, dust residues, allergenic dyestuffs, nickel or other contaminants and pH measurement to ensure that the surface pH is between the normal human skin physiological range, even should surface components react with sweat or saliva.

If the article is a soft toy, it undergoes the above tests and an additional test to detect any pile/fur loss.

If the article is unsuitable for washing at a temperature of 55° C. or above, then the method includes the step of holding the article at a temperature below 0° C. for a time sufficient to kill the dust mites prior to the washing step.

If the article successfully passes through the testing and washing stages, the article can be certified to safely withstand cleaning at home a designated number of times under specified wash conditions to maintain a low allergen level without deteriorating in quality or safety.

The desired target for allergen levels is an amount which does not trigger an allergic response in a susceptible person. According to World Health Organisation guidelines, this amount should not exceed 10 micrograms of allergen per gram of dust. The present invention is aimed at retaining allergen levels at below 2 micrograms per gram dust to avoid the possibility that an individual may become sensitised to the allergen.

In the present invention, quality control operating procedures are combined with traditional laboratory procedures. The present invention is suitable for use with any article that provides a breeding ground for the house dust mite or that can attract and retain household allergens. Generally such articles will conform to European Standard EN 71.

If the articles being tested are new articles, advantageously these may be initially passed through an optional pre-testing sequence to determine the level of a group of known allergens and/or irritants. Ideally the group incorporates the following non-exhaustive list of known allergens and/or irritants:

Microbiological contaminants including inter alia prokaryotic and eukaryotic microorganisms Formaldehyde pH values outside of the human skin physiological range of 7.35 to 7.45 either before or after reaction with saliva or sweat Dirt residues;

Allergenic dyestuffs

Nickel

Ideally the articles are tested to World Health Organisation (WHO) standards to ensure that they do not contain any of the group of recognised allergens carried over from their production. If the article is pre-certified by its manufacturer as free of the contaminants, then the optional pre-tests may be omitted.

Advantageously, on passing the pre-test sequence the new articles are artificially seeded with the house dust mite under controlled conditions. The seeding mites are bred in a laboratory by selecting an adequate diet, ensuring the microclimate is maintained at optimum levels, preventing contamination by fungi or any other mites and regular subculturing to prevent overcrowding. For exemplary purposes only, the house dust mite, *Dermatophagoides pteronyssinus* was used in the tests described herein. However, any common house dust mite species may be used for the purpose of this invention. Preferably, once a culture of known age is prepared the number of mites per gram in the culture is determined.

Advantageously, an article is seeded by either rolling it on a culture plate with a known amount of mites or by simply distributing a known amount of mites and culture medium over the surface of the article and gently brushing it in. Alternatively, the article can be seeded naturally by placing it in a domestic or work environment in which mites occur naturally, such as a bed. It is preferable to seed at least six identical articles to ensure there will be enough samples for testing and control purposes. Whilst there are many accepted methods to artificially seed articles, the method of choice will be dependent on the size and dimensions of the articles being seeded and will be known to a person skilled in the art. Ideally, once an article has been seeded the article can then be subjected to 'accelerated infestation'. The term 'accelerated infestation' describes a procedure where an article is infested with known levels of the house dust mite and then incubated at 20 to 25° C. and 70 to 75% relative humidity for up to twenty one days. This allows the allergens to build up to levels that would normally take up to three months to accumulate in a typical home environment. Whilst this is one method to rapidly accelerate the house dust mite level, other methods can also be used. Once the article has been seeded to the desired level, various allergen removal methods can be tested to discover a suitable and effective removal means for the article in question which does not damage that article. For example, studies have shown that a wash water temperature of 55° C. is the minimum effective temperature to kill the common house dust mite. Freezing together with low temperature washing has been found to be an effective alternative method to eradicate the house dust mite and associated allergens from household articles. Thus the house dust mite and its allergens can be eradicated using one of the outlined methods.

The house dust mite is commonly extracted from articles incorporating fibres by means of a vacuum cleaner with a filter placed in a receptacle in the hose. Dust mites and allergens are collected on the filter. The efficiency of this method is usually limited by the smallest filter pore size usable as air resistance increases with reduced pore size and amount of dust collected. Variations in sampling intensity may affect the ratio of the number of live mites to the amount of dust resulting in a lower number of live mites per unit weight of dust with more vigorous sampling. There are alternative methods used to extract the house dust mite, for example a pump mechanism could be used as opposed to a vacuum cleaner. Any means that will suitably remove the house dust mite can be used in the present invention.

It is preferable to ensure that there are no live mites remaining in the article after collection, and the ability of mites to cling to fibers thereby resisting their removal is known. Therefore, removal techniques were developed to take advantage of the natural mobility of the mites and their response to changes in local humidity and temperatures. This can be done by covering the surface of an article with an adhesive film and leaving it undisturbed for 24 hours, preferably in the dark. The film is then peeled off and the mites trapped on its surface are counted. Ideally, once the surface of the article is covered with the adhesive film, heat is applied to a side of the article away from the film. The house dust mites will move away from the source of the heat towards the adhesive film and become trapped.

Counting mites does not give an accurate quantitative estimate of allergen levels present in the environment. Allergens comprise up to 20% of the protein in house dust. Dust samples are normally used both for counting mites and for allergen quantification. Various immunochemical assays have been developed for quantification of mite allergens, including RAST inhibition, radioimmunoassay (RIA) and enzyme-linked immunosorbent assay (ELISA). ELISA is the most commonly used method. Monoclonal antibody based ELISA recognises just one single antigenic determinant on the allergenic protein. Therefore, when using this technique an assumption must be made that the ratio of the measured antigen to all other mite allergen remains constant.

Infestation by other species of mites, for example storage mites, which could also be a risk factor for symptoms, may remain undetected when monoclonal antibodies are used. Mite species cross-reactivity may be different with different monoclonal antibodies. Antibodies and monoclonal antibodies from different sources may give significantly different results. Polyclonal antibodies react to many antigenic determinants, and may bind to more isoforms and show broader cross-reactivity, but are less well defined than monoclonal antibodies. Samples are assayed against standards for accurate allergen quantification. If affinity chromatography with monoclonal antibodies has been used for allergen purification, only a few iso-allergens may have been purified and the standard curve will represent these isoforms, and not the total amount of allergen. Therefore, polyclonal antibodies may be better than monoclonal antibodies for these assays. The advantage of monoclonal antibody assays is their high reproducibility with regard to the performance of the antibodies, and the reliable availability of identical antibodies.

Ideally, once the article has been tested to validate removal of the mites/allergens, and the house dust mite and allergen level is deemed to be satisfactory, the article is prepared for entry into the quality control tests.

To remove mites and allergens, the article is washed in an automatic domestic washing machine at a specified temperature with specified detergent and dried according to specified procedures or the article is placed in a freezer bay, frozen for a minimum of 8 to 12 hours and put through a low temperature wash then dried in specified conditions. Both procedures are done in accordance with Method ISO 6330 Method 2A 60° C. and Method ISO 6330 Method 2A 40° C. respectively. Where the article is a soft toy, one of the toys will be cut open to remove it's stuffing and the stuffing also will be tested to ensure that the washing has removed allergens and mites from it. The article will be subjected to a specified number of cycles of washings termed 'durability washes', typically 12 for a soft toy, after which it is then subjected to a number of tests. The article may proceed through the washing cycles prior to undergoing some of the quality testing or as part of the test itself, where preconditioning/measurement is carried out initially. Ideally, if the article is a soft toy, the following tests are performed:

1) Colour Fastness;
2) Dimensional Stability;
3) Pile/Fur loss;
4) Stitching Failure; and
5) Visual Assessment If the article is not a soft toy, ideally, it is subjected to all of the above tests with the exception of (3) Pile/Fur loss. Excessive washing can affect the quality of an article, for example the colour or it can stain the surface material of a soft toy. Colour fastness is the resistance of colour textiles to different agents to which these materials may be exposed. Ideally, this is done by (a) visually assessing colour change and (b) using reflectance spectroscopy in accordance with British Standards BS1006: 1990, A02, EN ISO 105-A05, 1997.

Dimensional change is where excessive washing has affected the shape of an article, sometimes causing deformation. Ideally, the article is measured prior to commencing one of the outlined washing procedures and immediately after the washing procedure has been completed.

Loss of Pile/Fur from soft toys can be determined by the test outlined in BSI 4655:1986.

Preferably, stitching failure is tested using a tensile testing machine where the article is secured and subjected to a specified force, which pulls in equal and opposite directions causing a strain on the stitching. It should be done according to EN 71.

Ideally, Visual Assessment allows the tester to examine the article as a whole and determine whether or not there are obvious discrepancies between the article in its original state and a like article that has been subjected to the quality control tests.

The invention has particular application to the assurance of dust mite allergen control in household articles, toys and the like and more particularly to (1) articles which have a higher risk of allergen accumulation as they are textile or have a fibrous nature or component and (2) articles which are used habitually or frequently by individuals at higher risk of developing allergic responses, especially children and especially in the bedroom. Using the method of the invention it is possible to develop washing/cleaning procedures, which are easy to follow and apply in a domestic situation. A judgment can be as to how often the particular article would need to be decontaminated of allergens during its normal useful lifetime. The article is then subjected to that number of infestation/washing cycles and examined after each cycle to ensure that an acceptable article integrity and safety is retained and that allergens are removed. Once the article has passed testing, it can be offered for sale to domestic customers with an assurance or certificate that the article can safely withstand being cleaned at home a certified number of times under specified wash conditions to maintain low allergen levels and to maintain safety of the article per se. It will be appreciated therefore that the invention will have particular application in the area of articles commonly used by children and persons who are susceptible to allergen-triggered conditions.

As well as conducting the "accelerated infestation", sample articles are subjected to natural infestation and washing cycles to ensure that the article behaves similarly in the natural environment as in the faster laboratory tests. Should the results differ in the natural environment from the laboratory results, the certification of the article based on the laboratory results may need to be withdrawn or modified subsequently.

The invention is of notable benefit to retail groups, for example those selling bedding, clothes and toys including soft toys. The production of articles with certified evidence that they have withstood the testing procedures outlined herein would provide a very significant selling point of major commercial and healthcare value. Consumers will have great interest in buying an article that can be treated at home to help reduce the exposure of people, children in particular, to allergens while knowing at the same time that the article in question can safely withstand this treatment for a specified number of times, so that the article will retain its integrity and remain safe for its intended use.

The invention will hereinafter be described more particularly with reference to the accompanying drawings, which illustrate, by way of example only, the structure of and operational procedure of an embodiment of a testing procedure in accordance with the invention.

Whilst the following description refers in particular to the removal of house dust mites and their allergens from articles, it is to be understood that it is equally applicable to the removal of other allergenic material. Furthermore, it is to be appreciated that the methods described below at the same time remove mite and non-mite derived allergens from the article so that following treatment the article may be claimed to be allergenic free or reduced.

Figure 1:
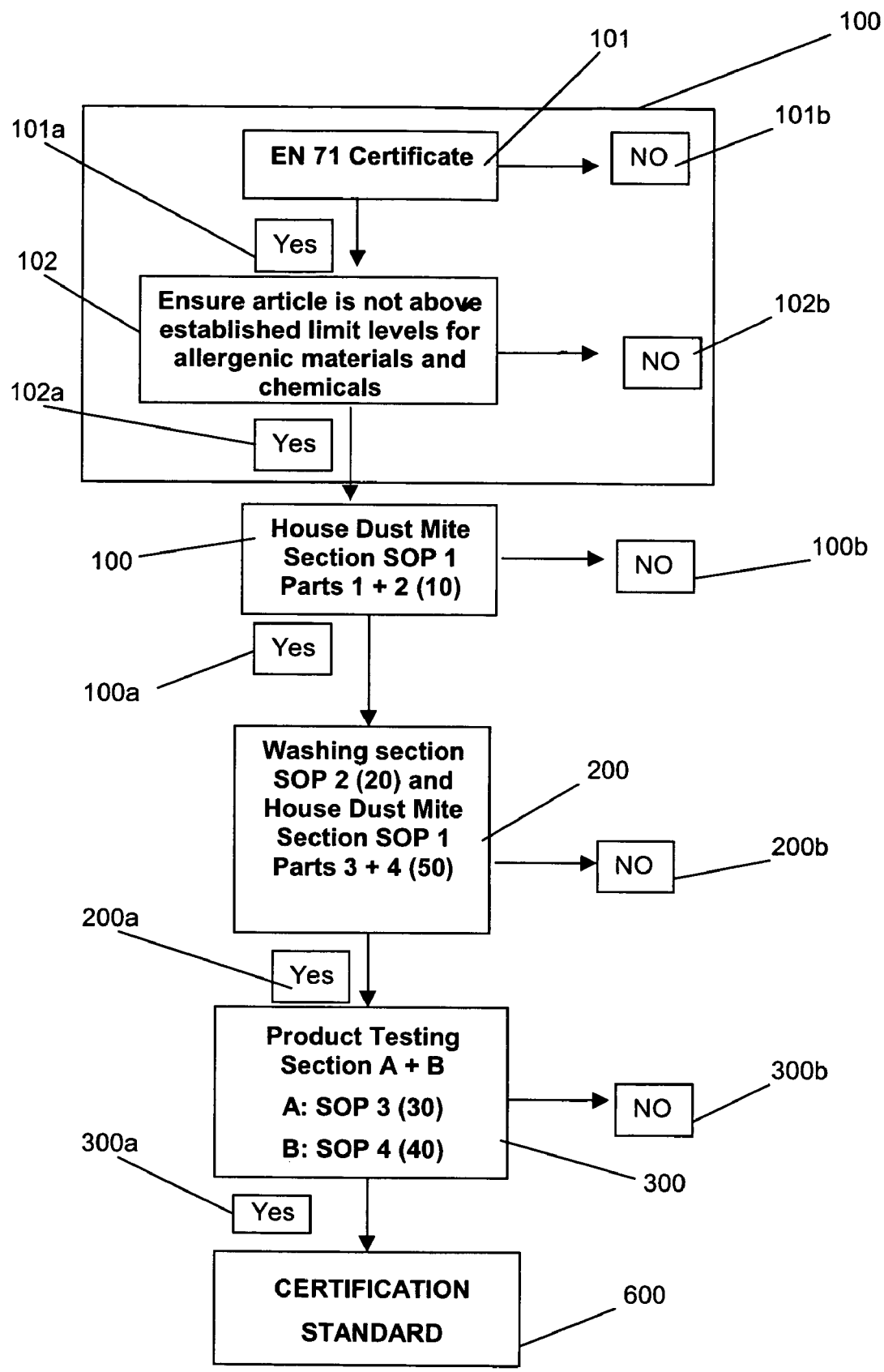
FIG. 1 is a flow diagram illustrating the overall structure of the procedure.

Referring initially to FIG. 1, there is shown an overview of the procedure according to the present invention. The testing procedure includes an optional pre-test sequence and four consecutive testing procedures. Initially the article being tested may be subjected to the optional pre-test sequence 1000 comprising two steps 101 and 102 respectively. The first step 101 establishes whether or not the article conforms to European Standard EN 71. If the article does conform 101a, it passes through to the next optional test 102, where levels of known allergens and/or irritants are determined. If the article does not conform 101b to European Standard EN 71, the article fails to continue through the pre-test sequence and subsequently will not enter the testing procedure for the certification standard.

In the optional step 102, when determining the level of known allergens and/or irritants present in/on the article, one or more of the following non-exhaustive group of known allergens and/or irritants are tested:

Microbiological contaminants including but not limited to bacterial and fungal contaminants;

Formaldehyde;

pH values outside of the human skin physiological range of 7.35 to 7.45 either before or after reaction with saliva or sweat;

Dirt residues;

Allergenic Dyestuffs such as azo dyes and the like; and

Nickel

The articles are tested to World Health Organisation (WHO) limit levels to ensure that they do not contain any of the above group of recognised allergens or irritants. If the article contains one or more of the above at a level that exceeds the WHO limit level for that particular allergen/irritant, the article will not enter the testing procedure for the certification standard 102*b*. In contrast if the article complies with the WHO limit level for each of the above allergens the article will proceed into the testing procedure for the certification standard 102*a*.

The article once it enters the testing procedure for the certification standard is submitted to 'accelerated infestation' with house dust mites using standard operating procedure one (SOP 1 Parts 1+2) 10, block 100. Assuming that the house dust mites infest the article 100*a*, the article proceeds to the next testing procedure.

The article undergoes one of two washing routines outlined in standard operating procedure two (SOP 2) 20 block 200. Once the washing routine is completed, tests are carried out to determine the levels of house dust mite or allergen in the article (SOP 1 Parts 3+4) 50, block 200. If the level of house dust mite in the article has failed to decrease after either or both of the hot or cold washing routines of standard operating procedure two (SOP 2) 20, block 200, the article is deemed unsuitable for certification and testing is terminated 200*b*. If the level of house dust mite in the article has decreased after the washing routine of standard operating procedure two (SOP 2) 20, block 200, the article proceeds 200*a* to the article testing section 300 to determine whether there has been any degradation in quality.

The article testing section is divided into two subsections 30 and 40 respectively and a given article will only proceed through one, depending on its nature. If the article is a soft toy, a cushion with pile or the like, it will then proceed through standard operating procedure three (SOP 3) 30, block 300, whereas all other article types will proceed through standard operating procedure four (SOP 4) 40, block 300. SOP 3 30, block 300 is also known as the Soft Toy Assessment Routine STAR. Essentially the standard operating procedures 3, 30 block 300 and 4, 40 block 400 are quality control tests determining how various aspects of the article were affected, if at all, by the washing routine carried out in SOP 2, 20, block 200. If there is degradation in the quality of either a toy or any other article the toy or article fails to proceed through the quality control tests 300*b* and is not awarded the certification standard. In contrast if the toy or article proceeds through the quality control tests 300*a* the toy or article is awarded the certification standard 600.

Figure 2:
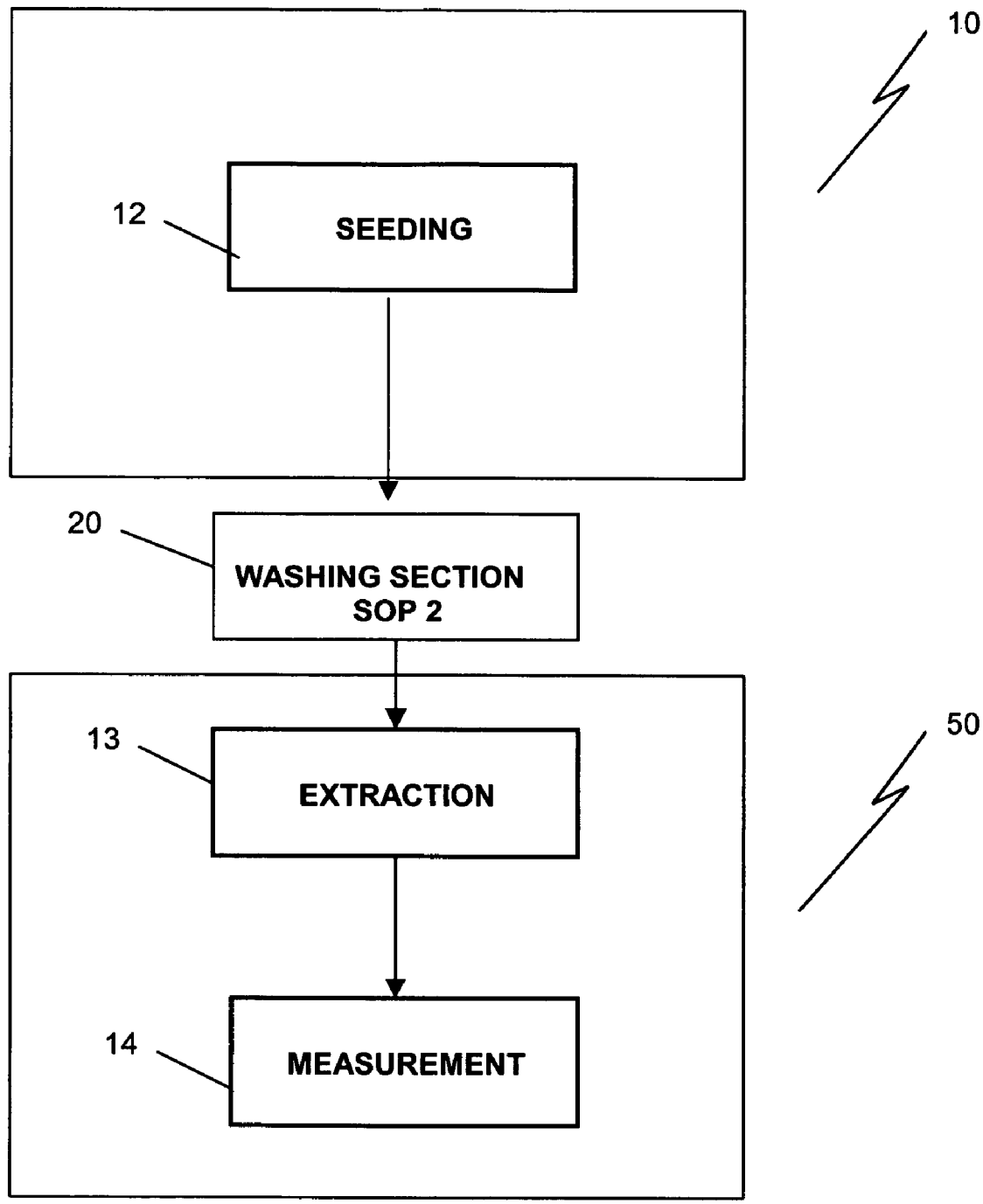
FIG. 2 is a flow diagram illustrating the breakdown of the first set of standard operating procedures.

FIGS. 2 to 5 show a more detailed breakdown of the standard operating procedures outlined in FIG. 1. FIG. 2 is a breakdown of the standard operating procedure one (SOP 1) block 10+block 50. The house dust mite (*Dermatophagoides pteronyssinus*) are bred from cultures. Mites live in their food, therefore the particle size of the culture medium can be important in determining population growth rates. The house dust mites are given a diet of a 1:1 mixture of dried liver (OXOID) and brewers yeast that was finely ground in an electric coffee grinder. The diet/culture medium is carefully prepared, being both sterilised and humidified prior to use. The culture is maintained at room temperature (18°-22° C.) and 70 to 75% relative humidity. The culture is also aerated weekly to discourage a build up of carbon dioxide. Any suitable method of obtaining and breeding house dust mite cultures can be used. It is important to control the relative humidity as excessive humidity can encourage mould growth which is undesirable. If the culture starts getting excessively crowded it is necessary to sub-culture by transferring half a portion of the contents to a new dish and adding fresh culture medium to both.

Once a series of cultures of known age are prepared, the cultures are divided into 100 mg samples. One of the 100 mg samples is immersed in liquid nitrogen, the mites are killed and then counted under a stereobinocular microscope. The number of mites per unit weight is determined.

The article is then seeded, FIG. 2, block 12. In this example the article is a soft toy, however the present invention is not limited to soft toys, it is suitable for any article that can provide a breeding ground for the house dust mite.

Seeding Example 500 mg of live mites are placed with 3 g of fresh mite culture medium in a shallow tray. The live mites and medium are dispersed over the surface of the tray. The soft toy is gently rolled around the tray, covering the main sections. The medium is then evenly distributed on the toy by gentle brushing.

The soft toy is incubated for 21 days at 20 to 25° C. and 70 to 75% relative humidity, allowing the mites to settle and disperse within the toy. Whilst this is one method of introducing the mite onto the article, there are alternative methods known to those skilled in the art.

Figure 3:
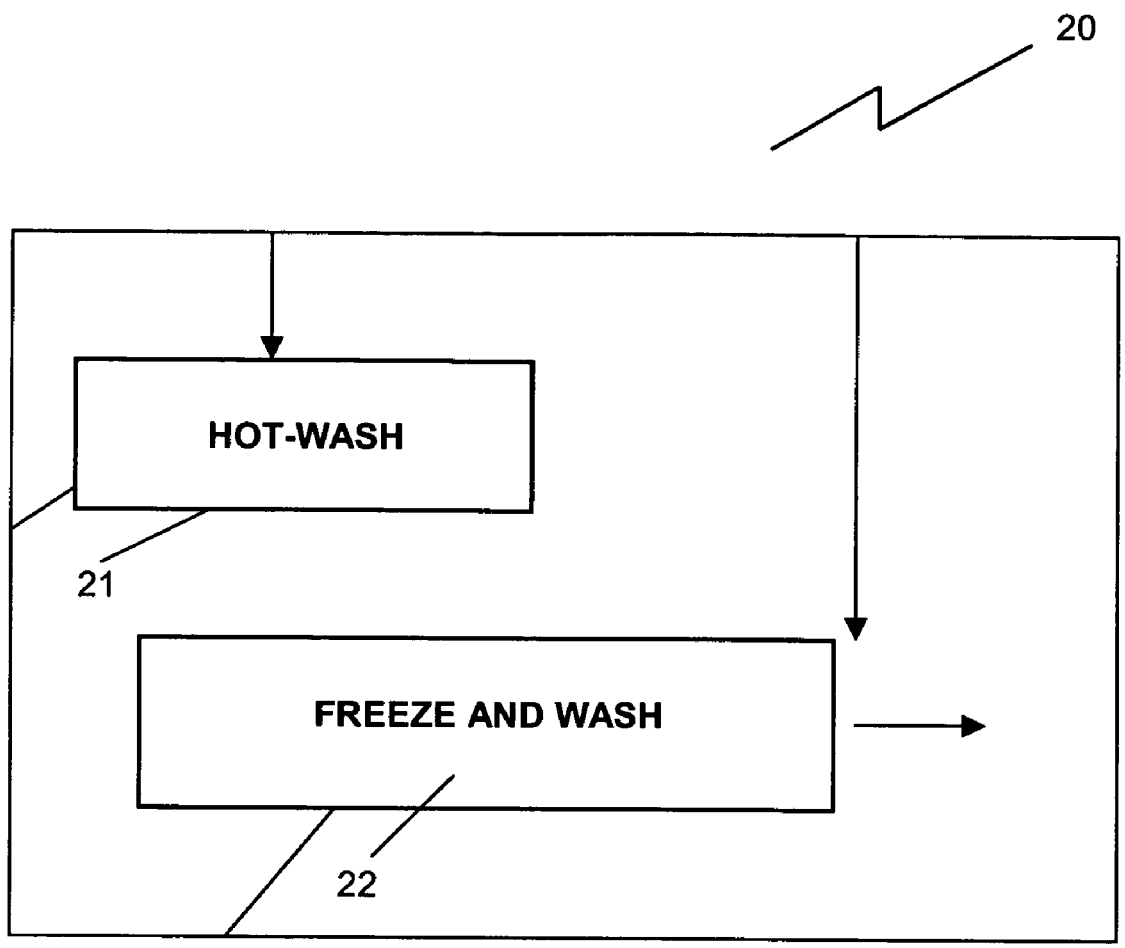
FIG. 3 is a flow diagram illustrating the breakdown of the second set of standard operating procedures.

After the article has been successfully seeded with the house dust mite, the house dust mite and allergen is removed using SOP 2 FIG. 2, block 20 by either washing at a temperature of 55° C. or above FIG. 3, block 21 or by freezing an article for at least 12 hours and then washing at a temperature lower than 55° C. FIG. 3, block 22. Either procedures can be used in this invention, and alternative methods that effectively remove the house dust mite can also be used.

The toy should be assessed and the most suitable method used.

Washing Section Example

1. Hot Wash/DrE: FIG. 3, block 21—

Method ISO 6330 Method 2A 60° C. is used. The test machine detergent and wash cycle are described in detail in this method. In order to stimulate the average wash cycle water of hardness 140±20° should be use with approximately 1-3 g of standard detergent per liter of water. The item once washed is then dried in a domestic dryer using a gentle drying cycle for 90 minutes or air dry in a drying cabinet at 45-50° C. to simulate a domestic airing cupboard.

2. Freeze/Cold Wash/Drv: FIG. 3, block 22—

Method ISO 6330 Method 6A 40° C. is used. The soft toy is placed in a labelled sealed polythene freezer bag and sealed. The bagged soft toy is placed in an eight cubic feet deep freezer (temperature −15° C. to −20° C.) for 24 hours. The bag is then removed, the soft toy is placed in a domestic washing machine and detergent (as above) is added. The item is then washed at a temperature of less than 55° C. Once the soft toy is washed, it is dried in a domestic drier, using a gentle drying cycle for 2 hours. After the Washing Section SOP 2, FIG. 2 block 20, has removed the house dust mite, it is necessary to determine the allergen/mite levels remaining in the article. Thus it is necessary to extract the remaining house dust mites, FIG. 2, block 13.

Extraction Example

There are a number of ways to extract the remaining house dust mite allergen. A combination of the techniques outlined below are used in the present invention and other methods are known to the skilled person.
(1) A standard hand held vacuum with an attached indoor biotech dust collection device is used. This consists of a filter tube that is inserted into the dust collector and the collector is pushed firmly onto the vacuum cleaner hose. The soft toy is vacuumed in a consistent manner for three minutes. The collector is then removed from the vacuum cleaner and sealed at the base. 0.05% Tween 20 in phosphate buffered saline pH 7.4 (PBS-T) is poured into the collector and the collector is sealed at the upper end. The collector is gently agitated for 1 minute. The extractant liquid is then poured off and centrifuged (18 to 20 mins, 2,500 RPM at 40° C.±2° C.). The supernatant liquid is removed and stored at −20° C.±2° C.
(2) Samples from the soft toy and unwashed control are cut into squares (5 cm×5 cm). The samples are then placed in petri dishes that have previously been lined with sticky autoclave tapes. The samples are left for 24 hours in the dark. The mites natural migration causes them to stick to the tape where they can then be counted.
(3) This involves using the petri dish in 2. The lid is removed and a foam pad (5 cm×5 cm) is placed directly above and in contact with the sample. Sticky autoclave tapes are adhered to the top surface of the foam pad.

The disk is heated from below remote the foam pad at a temperature of 30 to 35° C. The temperature is increased by 5° C. every 5 minutes until 90° C. is reached. The disk is left at this temperature for another hour. Any remaining mobile mites will move away from the heat through the foam pad and onto the sticky tapes.

The autoclave tapes from 2 and 3 are pressed onto a glass plate and examined under a binocular microscope. Any mites found are counted FIG. 2, block 14. The rate of inhibition of mite reproduction (MIR) of the treated sample is calculated in comparison with control sample using the following formula.

$$MIR\ \% = \frac{\text{Mean number of mites in control} - \text{mean number of mites in tests}}{\text{Mean number of mites in control}} \times 100$$

The tests are repeated either three or five times. If the tests are repeated three times the results are analysed in a subjective manner. With five repetitions simple comparative statistics can be performed.

The supernatant liquid that was obtained in (1) is analysed for allergen content using an ELISA plate, the values are obtained by inserting the readings observed into a software programme specifically designed for ELISA tests.

Figure 4:
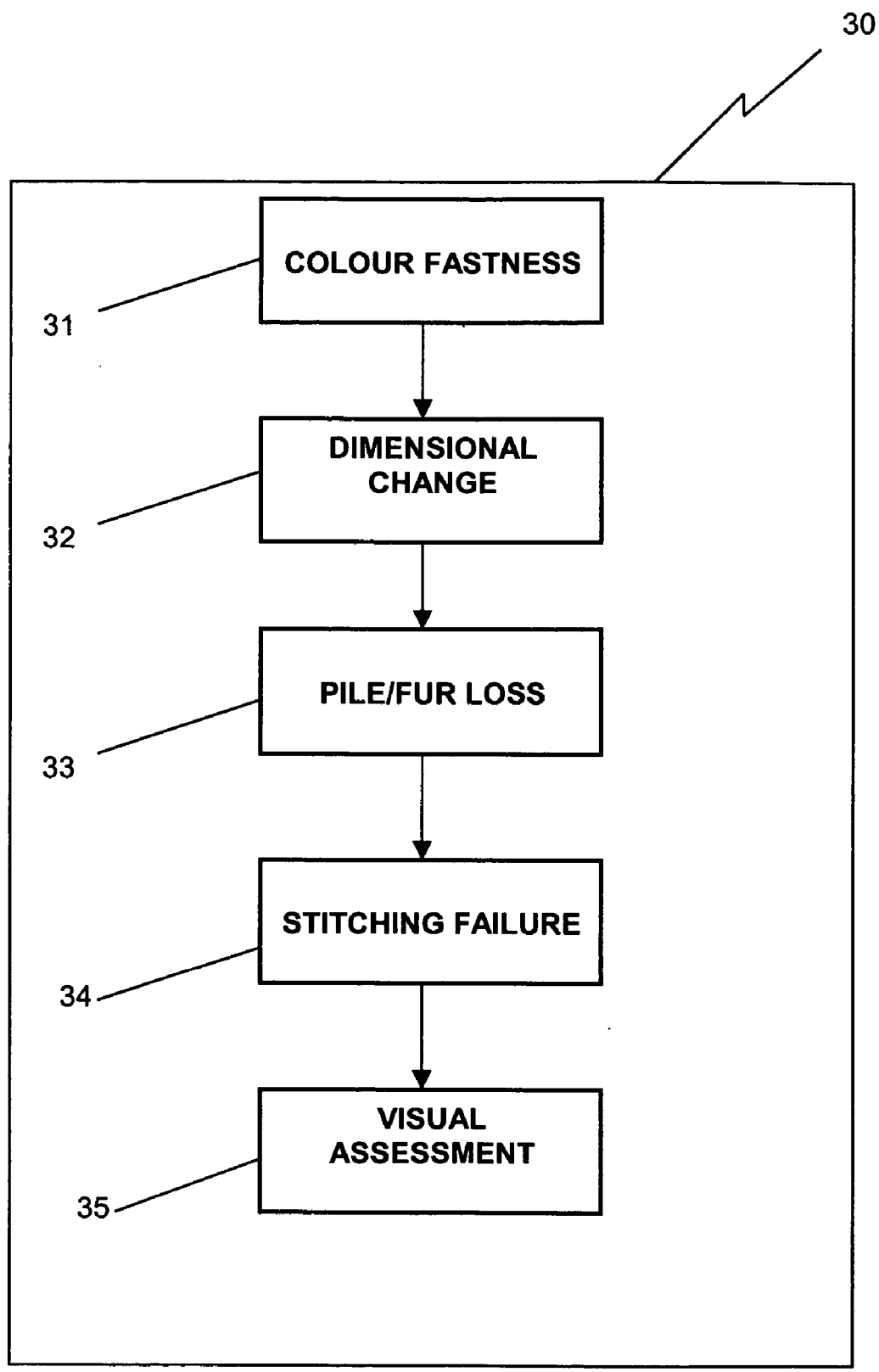
FIG. 4 is a flow diagram illustrating the breakdown of the third set of standard operating procedures.
Figure 5:
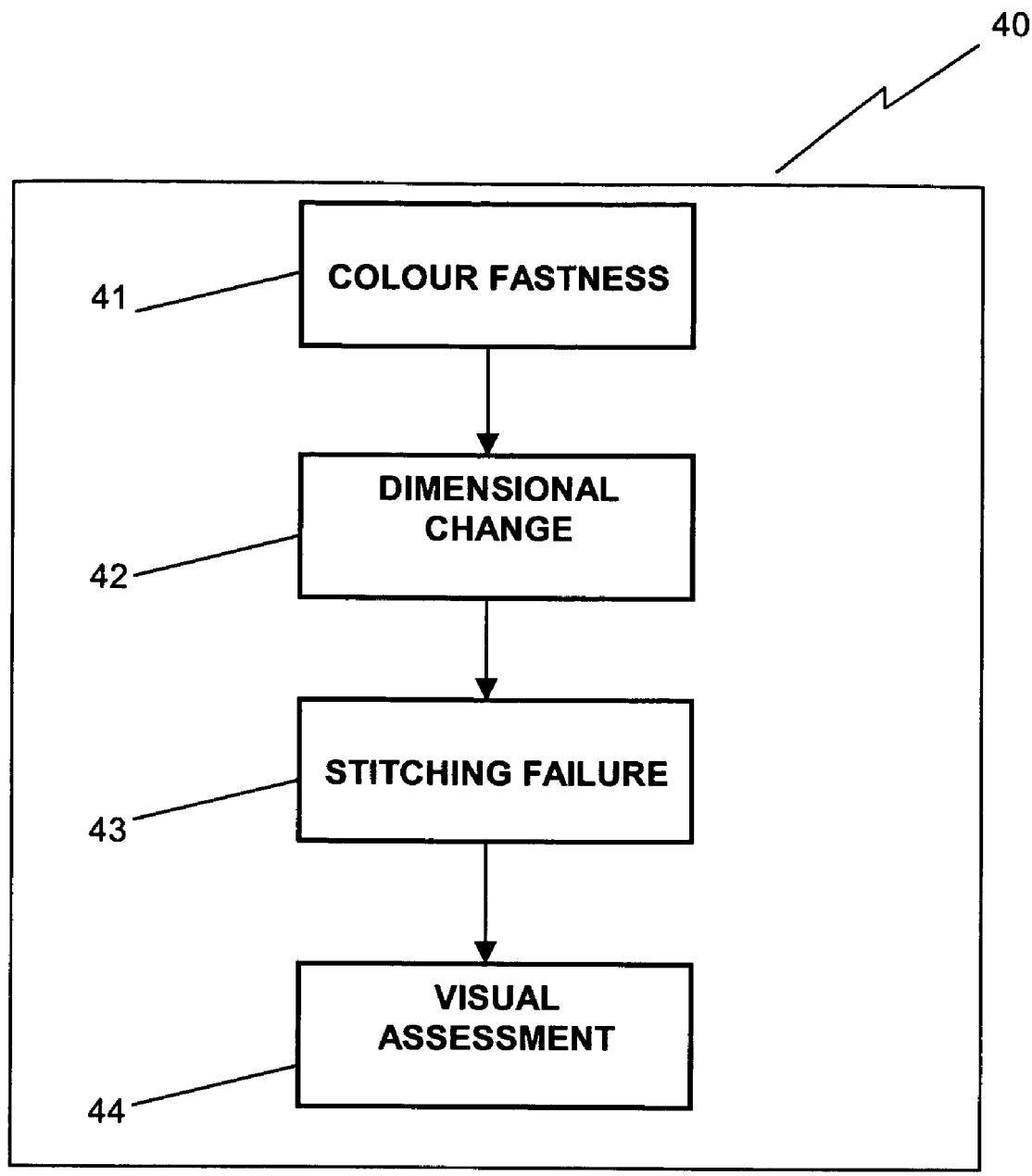
FIG. 5 is a flow diagram illustrating the breakdown of the fourth set of standard operating procedures.

FIGS. 4 and 5 illustrate quality control tests on the treated articles. If an article is a soft toy it will be tested according to SOP 3, FIG. 4, block 30, otherwise all articles are tested according to SOP 4, FIG. 5, block 40. The testing procedure is essentially the same with the exception of Pile/Fur loss test SOP 3, FIG. 4, block 33, which is not part of SOP 4, FIG. 5, block 40.

Colour Fastness

FIG. 4, block 31 and FIG. 5, block 41

The article must have completed at least 15 cycles of SOP 2 either a Hot Wash/Dry (FIG. 3, block 21) or Freeze/Cold Wash/Dry (FIG. 3, block 22). The cycles are carried out using detergents without optical brighteners. The soft toy as a whole is tested.

Colour fastness is determined using the following methods:
1. Visual assessment of Colour change; and Colour fastness to Washing at 60° C. and 40° C. (ISO 105 C06 C2S 60° C.) this test determines if the dyes cross stain other items in the wash.

Colour fastness to Washing (BS 1006 UK-TO) this test is for cotton and cotton blends only and determines if the dye is bleached by peroxy compounds in the detergents.

Colour Fastness to Water (ISO 105 EO I) this test determines if the dyes have a propensity to cross stain other items when wet e.g., from rain, saliva etc.

Colour fastness to Rubbing (ISO 105 X12) this test determines if the dyes rub off onto adjacent fabrics (e.g. denim onto furnishing fabrics).

Dimensional Stability

FIG. 4, block 32 and FIG. 5, block 42

Methods for assessing dimensional stability do not in general include dimensional changes occurring under tension. The soft toy as a whole is tested. The selection, dimensions, marking and measuring of test specimens are specified in ISO 3759. The area of the soft toy being measured is marked in millimeters and is longer than the greatest dimension being measured prior to washing. The soft toy is then washed at least 15 times according to the procedures outlined in SOP 2, FIG. 3, block 20. The area of the soft toy is then remeasured.

Pile/Fur Loss

FIG. 4, block 33

Excessive washing can cause the loss of pile/fur from soft toys and the extent of the effects can be determined by visual inspection. The general specified procedure for determining fur loss on soft toys is outlined in BSI 4655:1996.

The fabric is assessed under conditions of illumination specified in British Standard BS 950:Part 1 by direct comparison with an equivalent untested area of the same fabric, in particular, the boundary area between pile and non-pile sections of the fabric is assessed in accordance with Table 1.

TABLE 1

Pile Loss Rating

| Pile Loss Rating | Description |
| --- | --- |
| N | No Visible effect |
| I | Isolated single tufts of pile missing, giving rise to pinhole type of appearance |
| D | Small discrete areas devoid of several adjacent tufts of pile |
| C | A continuos band of pile removed from the specimen |

Stitching Failure

FIG. 4, block 34 and FIG. 5, block 33

Seams are assessed to EN 71 after the plurality washing process.

Visual Assessment

FIG. 4, block 35 and FIG. 5, block 44

Visual assessment allows the tester to examine the soft toy as a whole and to determine 5 whether or not there are obvious discrepancies between an original article and an article that has been prepared for the quality control test. See Table 2

TABLE 2

| Assessment | Comments |
| --- | --- |
| Shrinkage including differential shrinkage of component items and distortion | |
| Colour change and colour loss including abrasion | |
| Damage/white lines etc. | |
| Cross staining of colour onto other components | |
| Fraying of fabric and trims/stitching damage | |
| Detachment of fastenings and trims | |
| Damage to fastenings/zips, buttons, poppers including chipping and damage to coatings | |
| Loss/damaged prints | |
| Spirality/twisting | |
| Grinning/opening of seams | |
| Pilling/fuzzing of surface | |
| Pile loss or flattening | |
| Corrosion of metal components. | |
| Displacement of wadding and fillings | |
| Melting of components | |
| Delamination of fusing | |
| Any other significant change. | |

Figure 6:
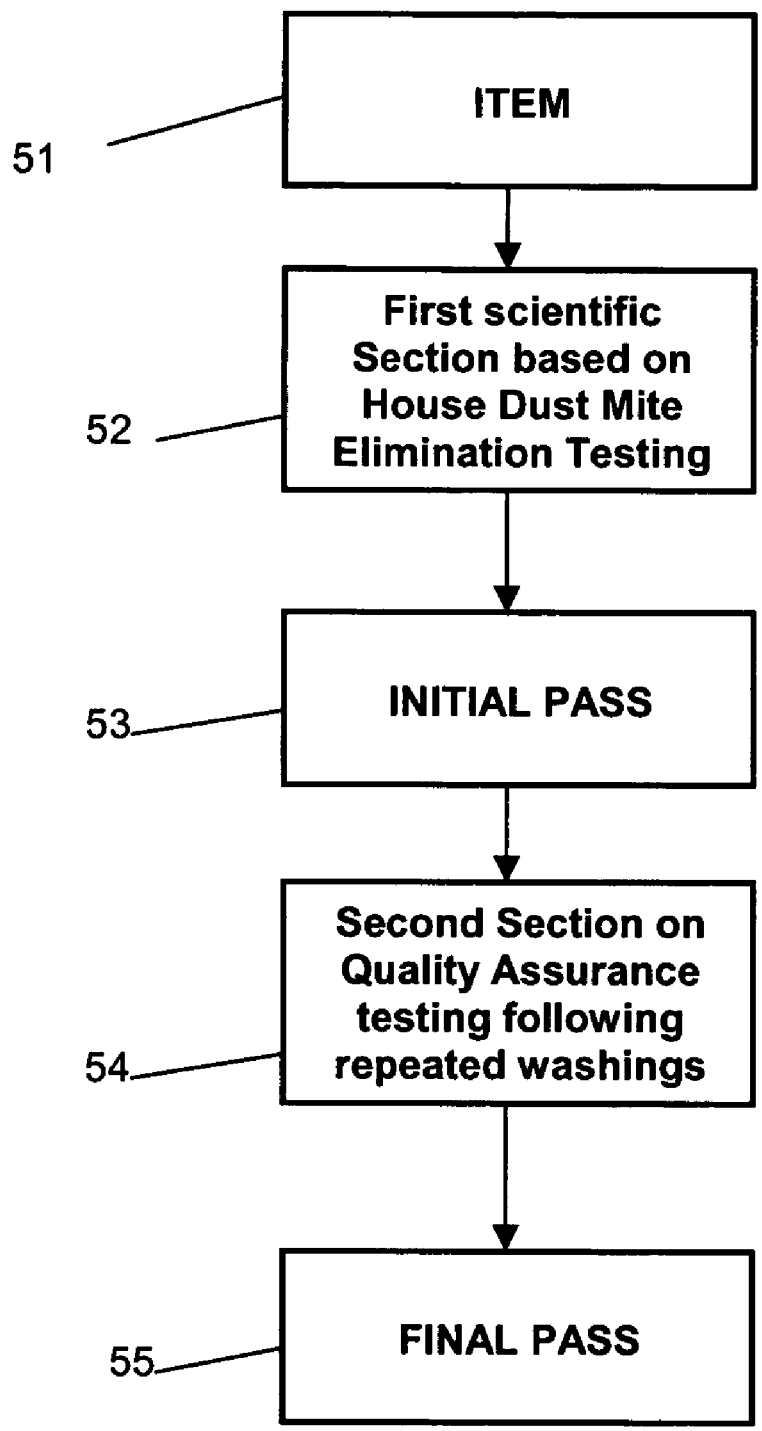
FIG. 6 is a flow diagram illustrating the overall structure of the testing procedure.

FIG. 6 is an overall view of the testing procedure. The article, block 51 is introduced to the first scientific section based on house dust mite elimination testing, block 52 where the level of house dust mite in the article after washing is determined. If this is successful the article passes the initial stage of the procedure, block 53 and enters the second section on quality assurance testing following repeated washings, block 54. If the article can sustain the number of washings without any deterioration it will pass through final stage, block 55. The article has then passed through a validated quality control testing sequence.

It will of course be understood that the invention is not limited to the specific details herein described, which are given by way of example only and that various alterations and modifications may be made without departing from the scope of the invention as defined by the appended claims.

The invention claimed is:

1. A method to certify a new manufactured article with respect to dust mite allergen removal and the integrity of said article, the method comprising the steps of
    (a) pre-testing the new manufactured article to detect the presence of dust mite allergens remaining from the manufacturing process;
    (b) seeding the article with a population of live mite species;
    (c) exposing the seeded article to environmental conditions that promote an accelerated growth of the live mite population;
    (d) after said accelerated growth, washing the article to remove mites and dust mite allergens from the article;
    (e) selecting a target level of dust mite allergens to remain after washing the article;
    (f) testing the washed article to determine the level of dust mite allergens remaining and whether the remaining level of dust mite allergens is below the target level;
    (g) if the remaining dust mite allergen level is below the target level, subjecting the article to a selected number of additional washings;
    (h) subjecting the article to at least one quality integrity test to determine if the article retains its integrity over a plurality of wash cycles; and,
    (i) in the event the quality integrity tests determine that the article retains its integrity during the additional washings, certifying the article with respect to dust mite allergen removal and the ability of the article to retain its integrity over a number of wash cycles under specified wash condition.

2. The method of claim 1 wherein in step (h) the quality integrity test is selected from a group consisting of colour fastness, dimensional stability, pile/fur loss, stitching failure, and visual assessment.

3. The method of claim 1 wherein in step (f) dust mite allergens are extracted from the article by covering a surface of the article with an adhesive film for a selected period of time.

4. The method of claim 3 wherein in step (f), after the adhesive film is applied to a surface of the article, heat is applied to the article remote from the film so dust mites migrate toward the heat and become trapped on the adhesive film.

5. The method of claim 1 wherein in step (c), the live mite population is exposed to the environmental conditions for up to twenty-one days.

6. The method of claim 5 wherein in step (c), the environmental conditions are a temperature of twenty to twenty-five degrees ° C. and a relative humidity of seventy to seventy-five percent.

* * * * *